United States Patent [19]

Hannah et al.

[11] Patent Number: 4,845,084

[45] Date of Patent: Jul. 4, 1989

[54] PHOSPHATE DERIVATIVES OF SUBSTITUTED BUTYL GUANINES, ANTIVIRAL COMPOSITIONS CONTAINING THEM, AND METHODS OF TREATING VIRAL INFECTIONS WITH THEM

[75] Inventors: John Hannah, Matawan; Richard L. Tolman, Warren, both of N.J.

[73] Assignee: Merck & Co., Inc., Rahway, N.J.

[21] Appl. No.: 54,457

[22] Filed: May 26, 1987

Related U.S. Application Data

[63] Continuation-in-part of Ser. No. 574,113, Jan. 26, 1984, abandoned.

[51] Int. Cl.$^4$ .......................... A61K 31/675; C07F 9/65
[52] U.S. Cl. ........................................ 514/81; 544/244; 544/84; 544/85; 544/86
[58] Field of Search .......................... 544/244; 514/81

[56] References Cited

U.S. PATENT DOCUMENTS

| | | | |
|---|---|---|---|
| 4,199,574 | 4/1980 | Schaeffer | 514/81 |
| 4,565,868 | 1/1986 | Verheyden et al. | 544/244 |
| 4,579,849 | 4/1986 | MacCoss et al. | 544/277 |
| 4,590,269 | 5/1986 | Prisbe et al. | 544/276 |
| 4,670,424 | 6/1987 | MacCoss et al. | 514/81 |

FOREIGN PATENT DOCUMENTS

| | | | |
|---|---|---|---|
| 0206459 | 12/1986 | European Pat. Off. | 544/244 |
| 0025358 | 7/1972 | Japan | 544/244 |
| 0332727 | 11/1977 | U.S.S.R. | 544/244 |

*Primary Examiner*—Donald G. Daus
*Assistant Examiner*—Diana G. Rivers
*Attorney, Agent, or Firm*—Richard S. Parr; Hesna J. Pfeiffer

[57] ABSTRACT

Phosphate derivatives of substituted butyl guanines which have antiviral activity against DNA viruses, such as herpes viruses and HTLV-III.

7 Claims, No Drawings

PHOSPHATE DERIVATIVES OF SUBSTITUTED BUTYL GUANINES, ANTIVIRAL COMPOSITIONS CONTAINING THEM, AND METHODS OF TREATING VIRAL INFECTIONS WITH THEM

The present application is a continuation-in-part of U.S. patent application, Ser. No. 574,113, filed Jan.26, 1984, now abandoned.

The present invention relates to phosphate derivatives of substituted butyl guanines, which have broad spectrum antiviral activity, particularly against the herpes family of viruses, e.g. herpes simplex virus, and against acquired immune deficiency syndrome (HTLV-III, AIDS).

BACKGROUND OF THE INVENTION

Pandit et al., in *Synthetic Communications*, 2(6), 345–351 (1972), disclosed the nucleoside analogue, 9-[4'-hydroxy-3'-(hydroxymethyl)butyl]giamome, but provided a method for preparing and analytical data for the biologically-inactive chlorohydroxy analogue, 9-(3'-chloromethyl-4'-hydroxymethyl)guanine. Other references by Hagberg et al. (U.S. Pat. No. 4,495,190), Ashton et al. (EPO Published Application No. 74 306), Verheyden et al. (EPO Published Application No. 85 424) and Schaeffer (U.S. Pat. No. 4,287,188) then relate to various other guanine and purine derivatives which have antiviral activity.

Continued interest in developing effective anti-herpes simplex agents and the increasing necessity to develop effective agents for the treatment and/or prevention of other DNA viruses, such as varicella-zoster, cytomegalovirus, Epstein-Barr virus and AIDS, has resulted in the development of the compounds of the present invention.

DESCRIPTION OF THE INVENTION

The compounds of the invention are represented by the formula:

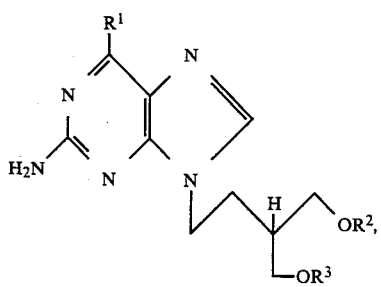
(I)

wherein $R^1$ is hydroxy, amino or halogen (i.e., fluorine, chlorine, bromine or iodine, preferably chlorine); and $R^2$ and $R^3$ are independently selected from hydrogen and a phosphate group having the formula:

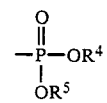

provided that $R^2$ and $R^3$ are not simultaneously hydrogen, or $R^2$ and $R^3$ taken together form a phosphate group having the formula:

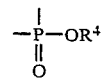

or a pyrophosphate group having the formula:

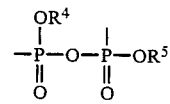

wherein $R^4$ and $R^5$ are independently selected from hydrogen, a pharmaceutically acceptable cation (e.g. sodium, potassium, magnesium, calcium, ammonium, or substituted ammonium such as $C_1$–$C_{10}$-alkylammonium), alkyl having 1 to 6 carbon atoms, phenyl or phenyl-$C_1$–$C_6$-alkyl.

The present invention also relates to important intermediates for preparing the above compounds. For example, compounds of the formula I wherein $R^1$ is benzyloxy, and $R^2$ and $R^3$ are each benzyloxy or are together isopropylidene.

In view of the above, it will be seen that one compound of the invention may be represented by the formula:

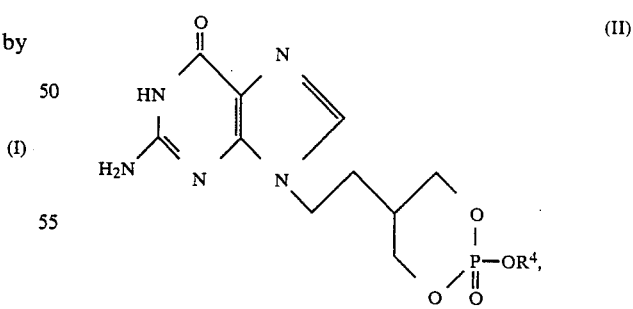
(II)

In the compound II, it will be seen that $R^2$ and $R^3$ form a phosphate group which taken together with the carbon atoms to which it is attached forms a 1,3,2-dioxaphosphorinane ring.

Preparation of the preferred cyclic phosphate derivative (II) is illustrated by the following reaction scheme:

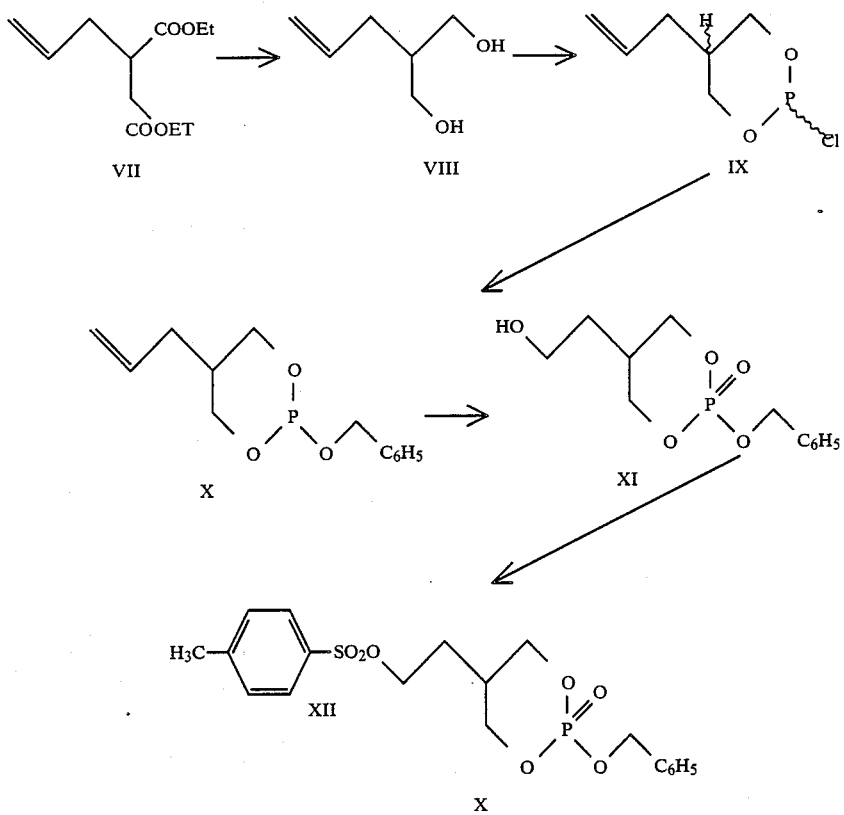

Compound VII is reduced to VIII which is then phosphorylated to give IX as a mixture of cis and trans isomers. Compound IX is then used to phosphorylate benzyl alcohol to form X. The allyl group of X is converted to the desired hydroxyethyl substituent by ozonolysis followed by reduction of the first formed aldehyde to alcohol. Simultaneously, the ozonolysis converts cyclic $P^{III}$ to $P^{V}$. The product XI which is still a mixture of cis and trans isomers, is converted to its tosyl derivative XII. From this mixture of cis and trans isomers, a single isomer can be separated by crystallization. The single isomer of XII is used to alkylate XIII yielding a mixture of the 9-isomer and 7-isomer which may be separated by chromatography. Deprotection of the desired 9-isomer by hydrogenation yields the biologically active cyclic phosphate monosodium salt XVI. The desired cyclic phosphate XVI may also be prepared by direct phosphorylation of the compound of formula I, wherein $R^2$ and $R^3$ are both hydrogen (which may be prepared by preliminary hydrolysis of the 6-chloro substituent of compound 20 of Pandit et al., *Synthetic Communications*, 2(6), 345–351 (1972), to an hydroxyl group, followed by catalytic hydrogenation of the benzyl protecting groups) using orthochlorophenylphosphorodichloridate followed by deprotection by standard hydrogenation conditions, for example, by hydrogenation with hydrogen gas in the presence of a noble metal catalyst, such as palladium or platinum.

The cyclic pyrophosphate may also be prepared from the diol by phosphorylation with phosphorous oxychloride to give the diol bismonophosphate disodium salt, followed by cyclization using dicyclohexylcarbodiimide to give the desired product as the disodium salt.

The following compounds are representative of the compounds of the present invention:

9-[4'-hydroxy-3'-(hydroxymethyl)butyl]guanine cyclic phosphate;

9-[4'-hydroxy-3'-(hydroxymethyl)butyl]guanine cyclic pyrophosphate;

9-[4'-hydroxy-3'-(hydroxymethyl)butyl]-2,6-diaminopurine cyclic phosphosphate;

9-[4'-hydroxy-3'-(hydroxymethyl)butyl]-2,6-diaminopurine cyclic pyrophosphate;

9-[4'-hydroxy-3'-(hydroxymethyl)butyl]-2-amino-6-chloropurine cyclic phosphate;

9-[4'-hydroxy-3'-(hydroxymethyl)butyl]-2-amino-6-chloropurine cyclic pyrophosphate;

9-[4'-hydroxy-3'-(hydroxymethyl)butyl]guanine monophosphate monosodium salt:

9-[4'-hydroxy-3'-(hydroxymethyl)butyl)-2,6-diaminopurine monophosphate monosodium salt; and 9-[4'-hydroxy-3'-(hydroxymethyl)butyl]-2-amino-6-chloropurine monophosphate monosodium salt.

The following compounds are preferred:

9-[4'-hydroxy-3'-(hydroxymethyl)butyl]guanine cyclic phosphate; and

9-[4'-hydroxy-3'-(hydroxymethyl)butyl]-2,6-diaminopurine cyclic phosphate.

These compounds are useful in the treatment and/or prevention of DNA viruses, particularly against herpes viruses, such as herpes simplex virus type 1, herpes simplex type 2, varicella-zoster, cytomegalovirus and Epstein-Barr virus, and against HTLV-III (acquired immune deficiency syndrome, AIDS) in mammals, particularly in humans.

In another aspect of the invention there is provided a pharmaceutical composition or preparation comprising a compound of formula (I), wherein $R^1$, $R^2$ and $R^3$ are as hereinbefore defined, or a pharmaceutically acceptable salt thereof, together with a pharmaceutically-acceptable carrier therefor. In a particular aspect the pharmaceutical composition comprises a compound of formula (I) in a therapeutically-effective unit dosage form.

As used herein the term "therapeutically-effective unit dosage" or "effective unit dose" is denoted to mean a predetermined antiviral amount sufficient to be effective against the viral organisms in vivo. Pharmaceutically-acceptable carriers are materials useful for the purpose of administering the medicament, and may be solid, liquid or gaseous materials, which are otherwise inert, medically-acceptable and are compatible with the active ingredients.

These pharmaceutical compositions may be given parenterally, orally, used as a suppository or pessary, applied topically as an ointment, cream, aerosol, powder, or given as eye or nose drops, etc., depending on whether the preparation is used to treat internal or external viral infections.

For internal infections the compositions are administered orally or parenterally at dose levels of about 0.1 to 250 mg per kg, preferably 1.0 to 50 mg per kg of mammal body weight, and are used in man in a unit dosage form, administered, e.g. a few times daily, in the amount of 1 to 250 mg per unit dose.

For oral administration, fine powders or granules may contain diluting, dispersing and/or surface active agents, and may be presented in a draught, in water or in a syrup; in capsules or sachets in the dry state or in a non-aqueous solution or suspension, wherein suspending agents may be included; in tablets, wherein binders and lubricants may be included; or in a suspension in water or a syrup. Where desirable or necessary, flavoring, preserving, suspending, thickening or emulsifying agents may be included. Tablets and granules are preferred, and these may be coated.

For parenteral administration or for administration as drops, as for eye infections, the compounds may be presented in aqueous solution in a concentration of from about 0.1 to 10%, more preferably 0.1 to 7%, most preferably 0.2% weight/volume. The solution may contain antioxidants, buffers, etc.

Alternatively for infections of the eye, or other external tissues, e.g. mouth and skin, the compositions are preferably applied to the infected part of the body of the patient as a topical ointment or cream. The compounds may be presented in an ointment, for instance, with a water-soluble ointment base, or in a cream, for instance with an oil in water cream base, in a concentration of from about 0.1 to 10%, preferably 0.1 to 7%, most preferably 1% weight/volume.

The following non-limiting Examples illustrate the preparation of compounds and compositions of the present invention, with all temperatures being in ° C.

EXAMPLE 1
9-[4'-Chloro-3'-(hydroxymethyl)butyl]guanine

9-[4'-Benzyloxy-3'-(benzyloxymethyl)butyl]-6-chloropurine (see Pandit et al., cited above) (300 mg) was dissolved in a mixture of ethanol (6 ml) and aqueous 2N HCl (6 ml) and the clear solution heated to boiling in an oil bath. The ethanol was gradually distilled out in approximately 30 minutes, then reflux/slow distillation of the residual aqueous 2N HCl solution was continued with the oil bath at about 140°. After 3 hours, the solution volume was reduced to about 2 ml. An aliquot was resolved on thin layer chromatography [silica gel:CHCl$_3$/aqueous 90% methanol/acetic acid (60:40:0.1)] and the reaction was determined to be incomplete. The reaction solution was diluted with more aqueous 2N HCl (2 ml) and the solution was boiled under reflux for 2 more hours and then evaporated to dryness, first in a stream of $N_2/100°$ then at 100°/0.5 mm. The crude product was a pale brown foam/glass (204 mg).

Preparative reverse phase liquid chromatography using a 0.94×50 cm octadecylsilanoxysilica (Partisil Magnum 9-ODS-2) column and 20% aqueous methanol with 40 mg portions of the reaction mixture and UV detection at 290 nm gave a good resolution of four materials. The two major products were recrystallized from hot water and their structures assigned by mass spectroscopy and 200 MHz nuclear magnetic resonance spectra. The UV spectra of the two materials showed them to possess the guanine chromophore.

Fraction 2 was identical to the title compound of Example 3 by mass spectral and NMR criteria; m.p. 273°–275°. The mass spectral and NMR data were as follows:

MS (fast atom bombardment (FAB)): M+H=254.
NMR (D$_2$O)w: 1.68 (m, 1H

1.89 (dt, 2H, J=7 and 7Hz,

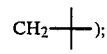

3.64 (d, 4H, J=6Hz, (—CH$_2$O—)$_2$); 4.18 (t, 2H, J=7Hz, N—CH$_2$); 7.88 (s, 1H, C$_8$—H).

Fraction 4 was shown to possess a covalent chlorine atom by the mass spectral studies and the structure of Formula IV (above) was assigned on the basis of the UV and NMR spectra examination. The melting point was 178°–182°; in good agreement with the only definitive physical characterization value published by Pandit et al. The mass spectral, ultraviolet spectral and NMR data were as follows:

MS (FAB): M+H, double peak=272 and 274.
UV: λ max 252 nm.
NMR (D$_2$O)δ: 1.94 (m, 3H

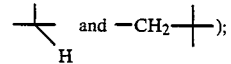

3.66 (d, 2H, J=5Hz, —CH$_2$Cl); 3.72 (d, 2H, J=5Hz, —CH$_2$O—); 4.19 (t, 2H, J=7Hz, N—CH$_2$); 7.89 (s, 1H, C$_8$—H).

EXAMPLE 2
9-[4'-Benzyloxy-3'-(benzyloxymethyl)butyl]guanine

9-[4'-Benzyloxy-3'-(benzyloxymethyl)butyl]-6chloropurine (377 mg) was dissolved in ethanol (10 ml) and aqueous 2N HCl (5 ml) was added. The clear solution was then heated to 80° in a loosely stoppered flask. After 8 hours the reaction was determined to be complete by thin layer chromatography [silica gel:CHCl$_3$/aqueous 90% methanol (90:10)]. The reaction solution was evaporated to dryness at 80°/0.5 mm leaving a yellow gum (385 mg) which was crystallized from hot water (4 ml)/ethanol (1 ml) yielding colorless leaflets (252 mg), m.p. 210°-224°. Two recrystallizations from hot ethanol gave pure product with m.p. 218°-222° (237 mg, 65%).

NMR(D$_2$O)δ1.83 (broad s, 3H,

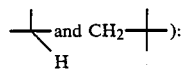 and CH$_2$—):

3.44 (m, 4H, (—CH$_2$—O—)$_2$); 4.02 (t, 2H, J=6Hz, N—CH$_2$); 4.44(s, 4H, —OCH$_2$Ph); 6.43 (s, 2H, —NH$_2$); 7.34 (m, 10H, Ar); 7.70 (s, 1H, C$_8$—H).

EXAMPLE 3

9-[4'-Hydroxy-3'-(hydroxymethyl)butyl]guanine

The addition of p-toluenesulfonic acid monohydrate (83 mg) to a magnetically stirred suspension of 9-[4-benzyloxy-3-(benzyloxymethyl)butyl]guanine (190 mg) at 22° in methanol (5 ml) gave a clear solution to which 20% Pd(OH$_2$)/C catalyst (38 mg) was added. The mixture was then hydrogenated at room temperature and pressure. After 60 minutes the reaction was complete by thin layer chromatography (silica gel:CHCl$_3$: aqueous 90% methanol [70:30]). Water (2 ml) was added to the reaction mixture which was then titrated to pH=7.0 with aqueous 2N NaOH (about 0.32 ml). Most of the methanol was evaporated from the mixture at 70°/100 mm and the hot residual aqueous mixture was filtered through diatomaceous earth (Supercel), with hot water (2×½ ml) washing. The clear filtrate was evaporated at about 70°/100 mm to about 1 ml and allowed to crystallize, yielding colorless, matted leaflets (70 mg), m.p. about 250°-271°. Evaporation of the mother liquors at about 70°/0.5 mm left a colorless, sticky solid (247 mg) which was chromatographed over two 8"×8"2000 micron GF silica plates: CHCl$_3$/aqueous 90% methanol:50:50. The appropriate active area was thoroughly extracted with the same solvent yielding a colorless solid (59 mg) which was recrystallized from hot water (1 ml) to give colorless matted leaflets (19 mg), m.p. 268°-273°. The two crops were combined and crystallized from water to give colorless matted leaflets, m.p. 271°-275°. The NMR spectrum was identical to that set forth above in Example 1 for fraction 2.

EXAMPLE 4

5-[2'-(2-amino-1,9-dihydro-6-oxo-6H-purin-9-yl)ethyl]-2-hydroxy-2-oxo-1,3,2-dioxaphosphorinane Sodium Salt Step A: Diethylallylmalonate (96.00 g, 0.480 mole) was added dropwise over a period of 30 minutes, to 800 ml of a 1.0M solution of lithium aluminum hydride in tetrahydrofuran with vigorous magnetic stirring. The heat of reaction caused the mixture to boil under reflux. The mixture was stirred and allowed to cool to room temperature for one additional hour. Saturated aqueous NaCl (400 ml) was then added dropwise, again causing the mixture to boil under reflux. A reasonably granular inorganic precipitate was formed. The mixture was then cooled to room temperature and the supernatant layer was decanted through a sintered funnel. The inorganic material was shaken with two 200 ml portions of ether and the combined organic extracts were evaporated at about 60° (water bath temperature) at a pressure of 120 mm to yield a pale yellow oil. For drying, this oil was dissolved in 250 ml of ether and magnesium sulfate was added. After filtration, the supernatant was evaporated yielding a pale yellow oil (59.88 g) which was fractionally distilled through a 1×10 cm Vigreux column. The fraction having a boiling point of 85°/0.2 mm pressure (40.05 g), 2-allylpropane-3diol, was retained for use in the following step.

Step B: 2-Allylpropane-1,3-diol (20.00 g) and sieve dried triethylamine (34.84 g) were mixed. Anhydrous ether was then added to bring the volume of the solution (Solution A) to 100 ml. Freshly distilled PCl$_3$ (23.65 g) was dissolved in anhydrous ether to a solution volume of 100 ml (Solution B). Solutions A and B were added simultaneously, dropwise, at the same rate over a period of one hour to vigorously mechanically stirred anhydrous ether (400 ml) at 0° under dry nitrogen in an ice bath. Each portion reacted instantly, precipitating HN$^+$Et$_3$Cl$^-$ with the mixture becoming a thick slurry. Stirring was continued at 0° for an additional 30 minutes. The mixture was then filtered and the solids were washed with two 200 ml portions of ether. The combined ethereal filtrates were evaporated at about 50° (water bath temperature) and 100 mm pressure. The residue was a colorless oil (31.88 g) which was fractionally distilled through a 1×10 cm Vigreux column. The fractions boiling at 53°-61°/0.50 mm pressure were combined (18.72 g) and redistilled in the same apparatus. The fraction boiling at 42°-44°/0.15 mm pressure, a 3.2:1.0 cis:trans mixture of 5-allyl-2-chloro-1,3,2-dioxaphosphorinane (16.14 g) was retained for the next step. It has the following NMR spectrum:

|  | Cis | Trans |
| --- | --- | --- |
| \H/ Y | 2.45 m | 1.77 m |
| \\ CH$_2$ \ | 1.92 m | 2.56 m |
| OCH$_A$ | 4.00 m | 3.90 m |
| OCH$_B$ | 4.25 m | 4.78 m |
| H$_2$C \ / | 5.14 m | 5.14 m |
| \\ / Y H | 5.72 m | 5.72 m |

Step C: 5-Allyl-2-chloro-1,3,2-dioxaphosphorinane (1.000 g) was dissolved in anhydrous ether (5 ml) and added dropwise over a period of 10 minutes to a magnetically stirred solution of benzyl alcohol (628 mg) and sieve dried triethylamine (560 mg) in anhydrous ether (20 ml) at 0° under dry nitrogen in an ice bath. HNEt$_3^+$Cl$^-$ rapidly separated. The mixture was stirred at 22° for an additional 20 minutes and then filtered. The solids were washed with two 10 ml portions of ether and the combined ethereal solutions were evaporated at about 40°, at a pressure of 100 mm, yielding a cis/trans mixture of 5-allyl-2-benzyloxy-1,3,2-dioxaphosphorinane as a colorless oil (1.461 g). A few mg of this oil were retained for NMR and the rest of the sample was treated at once with ozone and sodium borohydride as described below. NMR showed that the trans:cis ratio was 3.17:1.

Step D: Freshly prepared 5-allyl-2-benzyloxy-1,3,2-dioxaphosphorinane (1.400 g) was dissolved in CH$_3$CN (28 ml) and 0.1 ml of a saturated solution of Solvent Red 23 dyestuff (Sudan III) in acetonitrile was added. The pale pink solution was cooled in a dry ice methanol bath at $-15°$ with magnetic stirring, and a stream of O$_2$/O$_3$ from a Welsbach T816 generator (8 lb/in$^2$; 90 volts; about ¼ liter/minute; about ¼ mmole O$_3$/minute) was bubbled through it venting through a tube filled with calcium chloride. After 42 minutes, the reaction solution was only very faintly pink and the O$_2$/O$_3$ was shut off. An excess of (CH$_3$)$_2$S (0.82 ml) was then added to the reaction solution and the $-15°$ cooling bath was replaced with a water bath at 30° for 15 minutes. With the reaction solution at about 23°, an excess of powdered sodium borohydride (0.210 g) was added in portions in about 2 minutes. Rapid reaction occurred and a colorless suspension formed which was stirred at room temperature for 20 minutes. The suspension was then cooled in an ice-bath and treated dropwise with a slight excess of a saturated solution of NaCl in aqueous HCl (about 5 ml). The mixture was diluted with 30 ml of chloroform, shaken, and the organic phase was decanted off from the wet opaque inorganic layer. The inorganic layer was extracted with decantation with 20 ml of chloroform and the combined chloroform solutions were dried over magnesium sulfate, filtered and evaporated at about 50°, at a pressure of 0.5 mm, leaving a very pale yellow viscous oil (1.405 g). This oil was chromatographed over a 2.2×10.5 cm column of silica gel (14 g), prepared in hexane/75% ethyl acetate as follows: The oil was shaken with 30 ml of hexane/75% ethyl acetate and a sticky paste formed. The supernatant was decanted onto the column. The paste was then extracted by decantation with three 10 ml portions and the column eluate collected as fraction 1 which was evaporated at about 60° at a pressure of 0.5 mm. This procedure was repeated with three 10 ml portions of various solvents as indicated below in Table I. After fraction 5, very little insoluble material was left.

TABLE I

| Fraction | Volume | Solvent | Material After Evaporation |
|---|---|---|---|
| 1 | 60 | hexane/75% ethyl acetate | trace gum (14 mg) |
| 2 | 30 | hexane/75% ethyl acetate | colorless oil (233 mg) |
| 3 | 30 | hexane/75% ethyl acetate | colorless oil (131 mg) |
| 4 | 30 | ethyl acetate | colorless oil (15 mg) |
| 5 | 30 | ethyl acetate/10% methanol | colorless oil (8 mg) |
| 6 | 30 | ethyl acetate/10% methanol | colorless oil (516 mg) |
| 7 | 30 | ethyl acetate/10% methanol | colorless oil (167 mg) |
| 8 | 30 | ethyl acetate/10% methanol | colorless oil (7 mg) |

Fractions 2 and 3 identical by thin layer chromatography on silica gel using hexane/75% ethyl acetate as the solvent. Similarly, fractions 6 and 7 were determined to be identical. NMR indicated that fractions 6 and 7 were the desired 2-benzyloxy-5-(2'-hydroxyethyl)-1,3,2-dioxaphosphorinane as a 2.6:1 trans:cis mixture and that fractions 2 and 3 were 5-allyl-2-benzyloxy-2-oxo-1,3,2 dioxaphosphorinane as a 3:1 trans:cis mixture. The latter compound is the result of incomplete ozonization where only P$^{III}$ has been oxidized to P$^V$.

Step E: Recrystallized para-toluenesulfonylchloride (479 mg) was added to a solution of 2-benzyloxy-5-(2'-hydroxyethyl)-2-oxo-1,3,2-dioxaphosphorinane (570 mg) in sieve-dried pyridine (1.5 ml) at 0° (ice bath) and the solution was magnetically stirred under dried nitrogen for three hours. The solution became a pale yellow slurry. Thin layer chromatography on silica gel with ethyl acetate as the solvent indicated that the reaction was incomplete. Accordingly, additional para-toluenesulfonylchloride (40 mg) was added to the reaction mixture, which was then allowed to warm up to 22° over a period of 30 minutes, becoming a clear yellow solution. Once again, thin layer chromatography indicated that the reaction was incomplete. After an additional 50 minutes at 22°, the solution was shaken with a mixture of 5 ml of ethyl acetate and 0.5 ml of water for 1 minute. An additional 25 ml of ethyl acetate was then added. The solution was then extracted in sequence with two 5 ml portions of water, two 5 ml portions of aqueous 1N hydrochloric acid, 5 ml of aqueous 5% sodium bicarbonate and 5 ml of water. The solution was then dried over magnesium sulfate, filtered and then evaporated at 60° at a pressure of 0.5 mm, yielding a colorless gum (503 mg). NMR, using CDCl$_3$, indicated that the material appeared to be a cis/trans mixture of the desired product. On standing at room temperature overnight, the crude product partially crystallized. Triturating the crude product with petroleum ether or diethyl ether gave gummy products. With 0.5 ml of ethanol, however, a finely divided solid was formed. The solid was filtered off, washed with two 0.2 ml portions of ethanol, and dried at 22° at a pressure of 0.5 mm to obtain 2-benzyloxy-5-(2-p-toluene-sulfonyloxyethyl)-1,3,2-dioxaphosphorinane as a colorless waxy solid (160 mg), m.p. 118°-121°. NMR (CDCl$_3$)w: 2.05 (m, 1H,

2.05 (t, 2H, J=5.5 Hz,

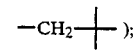

2.47 (s, 3H, TsCH$_3$); 4.07-4.22 (m, 2H, P—OCH$_A$—); 4.16 (t, 2H, J=5.5Hz, TsOCH$_2$—); 4.36-4.41 (m, 2H, P—OCHB—); 5.11 (d, 2H, J=8Hz, P—OCH$_2$Ph); 7.40 and 7.80 (ABq, 4H, J=8Hz, Ts); 7.43 (s, 5H, Ph).

Step F: 2-Amino-6-benzyloxypurine (113 mg) prepared as described in W. A. Bowles et al., J. Med. Chem., 6, 471 (1963), was dissolved in sieve-dried dimethylformamide (1 ml) at 23° forming a cloudy solution. This solution was treated with a 57% sodium hydride oil dispersion (24 mg). After several minutes of vigorous magnetic stirring, the oily clumps of the reagent slowly broke up with effervescence, forming a cloudy solution. 2-Benzyloxy-5-(2'-p-toluenesulfonyloxyethyl)-2-oxo-1,3,2-dioxaphosphorinane (200 mg) was added to the reaction solution at 23° dissolving rapidly with magnetic stirring under dry nitrogen. After three hours, a sample of the solution was tested by thin layer chromatography on silica gel with ethyl acetate/10% methanol as the solvent.

The reaction was found to be incomplete and was therefore allowed to continue overnight. The reaction solution was then diluted with 25 ml of ethyl acetate, washed with four 5 ml portions of water, dried over magnesium sulfate, filtered, and evaporated at 60° under 0.1 mm pressure, leaving a colorless glass (254 mg). This material was subjected to preparative thin layer chromatography on 2000 micron silica gel plates, using chloroform/aqueous 90% methanol, 80/20, as the solvent, followed by further preparative thin layer chromatography on 500 micron plates using the same solvent. Extraction of the band having R$_f$0.47 with chloroform/aqueous 90% methanol, 80/20, filtration, and evaporation at about 60°, under 0.5 mm pressure, yielded the 7-isomer 5-[2'-(2-amino-6-benzyloxy-7H-purin-7-yl)ethyl]-2-benzyloxy-2-oxo-1,3,2-dioxaphosphorinane (46 mg): NMR (CDCl$_3$): 1.45 (m 1H,

2 08 (dt, 2H, J=7.5 and 7.5 Hz

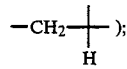

3.92 (m, 2H, J=20, (P), 11.5 (gem), 1 Hz, P—O—CH eq.); 4.15 (m, 2H, J=11.5 (gem), 4(P), 1 Hz, P—O—CH$_{ax}$); 4.20 (t, 2H, J=7.5 Hz, N—CH$_2$); 5.08 (d, 2H, J=8 Hz, P—O—CH$_2$Ar); 5.26 (s, 2H, NH$_2$); 5.47 (s, 2H, —OCH$_2$Ar); 7.34–7.43 (m, 10H, Ar); 7.77 (s, 1H, C$_8$—H). A mass spectrum of the silylated product showed m/e of 567 (i.e. 495+72).

Extraction of the band having R$_f$=0.60 with chloroform/aqueous 90% methanol, 90/10, filtration, and evaporation at about 60°, under 0.5 mm pressure, yielded the 9-isomer 5-[2'-(2-amino-6-benzyloxy-9H-purin-9-yl)ethyl]-2-benzyloxy-2-oxo 1,3,2-dioxaphosphorinane (72 mg) as a colorless foam. Crystallization from ethanol gave colorless prisms, m.p. 162°–166°. A mass spectrum showed a molecular ion of 495.1663 (calculated was 495.1672). NMR (CDCl$_3$)δ: 1.57 (m, 1H,

2.20 (dt, 2H, J=7 and 7Hz,

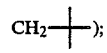

4.15 (t, 2H, J=7Hz, N—CH$_2$); 4.18–4.32 (m, 4H, m, P(OCH$_2$)$_2$); 4.99(s, 2H, NH$_2$); 5.10 (d, 2H, J=8 Hz, P—OCH$_2$Ar); 5.54 (s, 2H, OCH$_2$Ar); 7.29–7.52 (m, 10H, Ar); 7.59 (s, 1H, C$_8$–H).

Ultimate confirmation of structure was provided by single crystal X-ray crystallographic analysis, which showed the dioxaphosphorinane ring to be in the chair form, with the large 2,5-substituents trans and diaxial, and the attachment to the purine system to be at position 9.

Step G: 5-[2'-(2-amino-6-benzyloxypurin-9-yl)ethyl]-2-benzyloxy-2-oxo-1,3,2-dioxaphosphorinane (70 mg) was dissolved in methanol (5 ml) and 20% Pd(OH)$_2$/C catalyst (20 mg) was added. The mixture was hydrogenated with vigorous magnetic stirring at ambient temperature and pressure for 2 hours. The cloudy mixture was then filtered through Fisher diatomaceous earth (Celite) filter aid with additional washing with three 1 ml portions of methanol.

The catalyst and filter bed were then extracted with three 3 ml portions of water at 90°, spinning the solids down and decanting the hot supernatant through a fresh filter aid bed. The combined filtrates were evaporated at about 60° and 0.5 mm pressure, leaving a colorless crystalline solid (37 mg). This material was very sparingly soluble in D$_2$O but gave a good NMR spectrum for the desired product, 5-[2'-(2-amino-1,9-dihydro-6-oxo-6H-purin-9-yl)ethyl]-2-hydroxy-2-oxo-1,3,2-dioxaphosphorinane, plus some minor extraneous peaks at w5.8 and 7.5:

NMR (D$_2$O)δ:2.01(m, 1H,

2.02 (t, 2H, J=6 Hz,

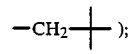

4.11 (ddd, 2H, J=12, 12 and 5 Hz, P—O—CH$_A$); 4.30(t, 2H, J=6Hz, N—CH$_2$—); 4.36 (ddd, 2H, J=2, 12 and about 2 Hz, P—O—CH$_B$); 8.69 (broad s, 1H, C$_8$—H).

In order to convert the above material to its sodium salt, 35 mg of material was suspended in 2 ml of distilled water at 23° and titrated from an initial pH of about 1 to pH 7.0 by adding aqueous 1N NaOH (88 microliters) slowly from a syringe. The solid readily dissolved. The solution was filtered and lyophilized yielding a colorless powder (38 mg): NMR (D$_2$O)δ: 1.95 (t over m, 3H, J=Hz,

plus

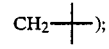

4.09 (ddd, 2H, J=12, 12, and 5 Hz P—O—CH$_A$); 4.17 (t, 2H, J=6Hz, N—CH$_2$); 4.33 (ddd, 2H, J=12, 12 and 2 Hz, P—O—CH$_B$); 7.97 (broad s, 1H, C$_8$—H) , plus minor unknown peaks at 5.58 and 7.46–7.56. Irradiation of δ1.95 to remove

and

simplified the spectrum to δ4.09 (dd, 2H, J=11.5 and 11.5Hz, P—O—CH$_A$); 4.17 (s, 2H, N—CH$_2$); 4.32 (dd, 2H, J=11.7 and 11.7 Hz, P—O—CH$_B$)

5-[2'-(2-Amino-1,9-dihydro-6-oxo-6H-purin-9-yl)ethyl]-2-hydroxy-2-oxo-1,3,2-phosphorinane was purified by reverse phase liquid chromatography using a 0.94×50 cm octadecylsilanoxysilica (Partisil M9, ODS-2) column as follows: 35 mg of the material to be purified was dissolved in about 470 microliters of water and successive injections were made of 50, 100, 100, 100 and 120 microliters. The eluant was aqueous 1% tetrahydrofuran at 5.0 ml/minute and off-maximum ultraviolet absorption at 295 nm was monitored. The dominant peak was collected at about 3 to 5 minutes. The combined eluates were lyophilized, yielding a colorless, fluffy solid (30 mg). The NMR spectrum was clean and sharp with no extraneous peaks, confirming purity of the product.

UV (0.01N NaOH):$\lambda_{max}$211, 251 and 270 nm.

EXAMPLE 5

9-(4'-Benzyloxy-3'-benzyloxymethyl)butyl-2,6-diamino-9H-purine

In a stainless steel bomb at 100° heat together 2-amino-9-(4'-benzyloxy-3'-benzyloxymethyl)butyl-6-chloro-9H-purine (1 g) and an excess of liquid ammonia (30 ml) for 20 hours. Allow the ammonia to evaporate and the non-volatile residue to be partitioned between CHCl$_3$ and water. Evaporate the dried CHCl$_3$ phase to small volume and chromatograph over a column of silica gel using an increasing gradient of methanol (0–20%) in the elution solvent (CHCl$_3$/MeOH). Monitor the eluate by UV absorbance and thin layer chromatography and combine and evaporate the appropriate fractions to give 9-(4'-benzyloxy-3'-benzyloxymethyl)butyl-2,6-diamino-9H-purine.

EXAMPLE 6

2,6-Diamino-9-(4'-hydroxy-3'-hydroxymethyl)butyl-9H-purine

Dissolve 9-(4'-benzyloxy-3'-benzyloxymethyl)butyl-2,6-diamino-9H-purine (200 mg) in methanol (10 ml) containing two equivalents of p-toluenesulphonic acid monohydrate (176 mg), and add 20% palladium hydroxide on carbon catalyst (50 mg). Hydrogenate the mixture at room temperature and pressure until an aliquot shows no starting material remaining by thin layer chromatography. Add water (5 ml), followed by aqueous 1N-NaOH until the acidic mixture is neutralized (pH=7). Evaporate off most of the methanol at 70°/100 mm and filter the hot aqueous phase through diatoaceous earth (Supercel) to remove the catalyst. Concentrate the filtrate at 70°/100 mm and allow the desired 2,6-diamino-9-(4'-hydroxy-3'-hydroxymethyl)butyl-9H-purine to crystallize.

EXAMPLE 7

9-[4'-Hydroxy-3'-(hydroxymethyl)butyl]guanine Mono and Bis Dibenzyl Phosphates

Suspend 9-[4'-hydroxy-3'-(hydroxymethyl)butyl]guanine (1.00 g) in anhydrous pyridine (100 ml) at 22° and treat with two equivalents of dibenzyl phosphorochloridate. Stir the mixture at ambient temperature for 20 hours and then evaporate to small volume (10 ml) at 30°/0.5 mm. Add chloroform (200 ml) and wash the solution with water (4×40 ml). Dry the organic layer over MgSO$_4$; filter; and evaporate at 60°/0.5 mm. Chromatograph the residue over silica gel in chloroform with increasing methanol content (0–10%) to elute first the bis dibenzyl phosphate and then the mono dibenzyl phosphate of the starting diol, obtaining the latter compound as a racemic mixture.

EXAMPLE 8 dl 9-[4'-Hydroxy-3'-(hydroxymethyl)butyl]guanine Monophosphate, and Monophosphate Monosodium Salt Suspend dl 9-[4'-hydroxy-3'-(hydroxymethyl)butyl]guanine monodibenzyl phosphate (100 mg) in methanol (20 ml) and add 20% Pd(OH)$_2$/C catalyst (20 mg). Hydrogenate the mixture at ambient temperature and pressure for 3 hours and then filter through Fisher diatomaceous earth filter aid (Celite) with additional methanol washing.

Extract the catalyst and filter bed with water (3×5 ml) at 90°, spinning down the solids and decanting the hot supernatant through a fresh filter aid bed. Evaporate the combined aqueous filtrates at 60°/0.5 mm leaving the desired diol monophosphate as a colorless crystalline solid. Convert this product to its monosodium salt by suspending it in water and adding one equivalent of aqueous 1N NaOH to approximately pH 6. Lyophilize the clear solution to give dl 9-[4'-hydroxy-3'-(hydroxymethyl)butyl]guanine monophosphate monosodium salt.

In an analogous manner, prepare 9-[4'-hydroxy-3'-(hydroxymethyl)butyl]guanine bis monophosphate and the derived bismonophosphate disodium salt.

EXAMPLE 9

| Oil in Water Cream Base | |
|---|---|
| 9-[4'-Hydroxy-3'-(hydroxymethyl)butyl]guanine | 5.0 g |
| Lanolin, Anhydrous | 20.0 g |
| Polysorbate 60 | 4.0 g |
| Sorbitan Monopalmitate | 2.0 g |
| Light Liquid Paraffin | 4.0 g |
| Propylene Glycol | 5.0 g |
| Methyl Hydroxybenzoate | 0.1 g |
| Purified Water to | 100.0 g |

Oil in Water Cream Base

EXAMPLE 10

| Water Soluble Ointment Base | |
|---|---|
| 9-[4'-Hydroxy-3'-(hydroxymethyl)butyl]guanine | 0.5 g |
| Glycerol | 15.0 g |
| Macrogol 300 | 20.0 g |
| Polyethylene Glycol 1500 | 64.5 g |

EXAMPLE 11

| Tablet - (Total weight 359 mg) | |
|---|---|
| 9-[4'-Hydroxy-3'-(hydroxymethyl)butyl]guanine | 100 mg |
| Lactose | 200 mg |
| Starch | 50 mg |
| Polyvinylpyrrolidone | 5 mg |
| Magnesium Stearate | 4 mg |

What is claimed is:

1. A compound of the formula:

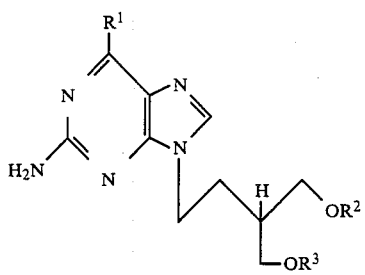

wherein $R^1$ is hydroxy, amino or halogen; and $R^2$ and $R^3$ are independently selected from hydrogen and a phosphate group having the formula:

provided that $R^2$ and $R^3$ are not concurrently hydrogen, or $R^2$ and $R^3$ taken together form a phosphate group having the formula:

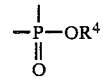

wherein $R^4$ and $R^5$ are independently selected from hydrogen, a pharmaceutically-acceptable cation, alkyl having 1 to 6 carbon atoms, phenyl or phenylalkyl wherein the alkyl moiety has 1 to 6 carbon atoms.

2. A compound according to claim 1, wherein $R^2$ and $R^3$ taken together form a phosphate group having the formula:

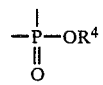

wherein $R^4$ is as defined in claim 1.

3. A compound according to claim 1, where $R^4$ and $R^5$ are the same.

4. 9-[4'-Hydroxy-3'-(hydroxymethyl)butyl]guanine cyclic phosphate, according to claim 1.

5. 9-[4'-Hydroxy-3'-(hydroxymethyl)butyl]-2,6-diaminopurine cyclic phosphate, according to claim 1.

6. An antiviral pharmaceutical composition comprising an effective amount of a compound according to claim 1 and an acceptable carrier.

7. A method of treating susceptible viral infections in mammals comprising administering to a mammal in need of such treatment an effective amount of a compound according to claim 1.

* * * * *